US012569636B2

(12) United States Patent  (10) Patent No.: US 12,569,636 B2
Gulliver et al.  (45) Date of Patent: Mar. 10, 2026

(54) NASAL CANNULA WITH TURBULATION ELEMENTS

(71) Applicant: Fisher & Paykel Healthcare Limited, Auckland (NZ)

(72) Inventors: Laurence Gulliver, Auckland (NZ); Mark Thomas O'Connor, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/181,356

(22) Filed: Feb. 22, 2021

(65) Prior Publication Data

US 2021/0308405 A1  Oct. 7, 2021

Related U.S. Application Data

(63) Continuation of application No. 15/022,451, filed as application No. PCT/NZ2014/000205 on Sep. 19, 2014, now Pat. No. 10,933,210.

(60) Provisional application No. 61/881,321, filed on Sep. 23, 2013.

(51) Int. Cl.
A61M 16/06 (2006.01)

(52) U.S. Cl.
CPC ..... A61M 16/0666 (2013.01); A61M 2206/11 (2013.01); A61M 2206/14 (2013.01); A61M 2206/20 (2013.01)

(58) Field of Classification Search
CPC .............. A61M 16/00; A61M 16/0672; A61M 16/0666; A61M 16/0461; A61M 16/04; A61M 16/0465; A61M 2206/14; A61M 2206/10; A61M 2206/11; A61M 2206/20; A61M 25/02; A61M 25/00; A61M 25/0021; A61M 25/0043; A61M 39/00; A61M 39/08
See application file for complete search history.

(56) References Cited

U.S. PATENT DOCUMENTS

| | | | |
|---|---|---|---|
| 3,643,660 A | 2/1972 | Hudson et al. | |
| 4,034,499 A | 7/1977 | Wild | |
| 4,621,953 A | 11/1986 | McGuth | |
| 4,621,983 A | 11/1986 | McGuth | |
| 6,019,753 A | 2/2000 | Pagan | |
| 7,087,027 B2 * | 8/2006 | Page ................... | A61B 5/0816 |
| | | | 600/537 |

(Continued)

FOREIGN PATENT DOCUMENTS

| | | |
|---|---|---|
| GB | 2465689 | 3/2011 |
| WO | WO2005/079726 A1 | 9/2005 |
| WO | WO2008/014543 A1 | 2/2008 |

OTHER PUBLICATIONS

International Search Report; PCT/NZ2014/000205; dated Dec. 22, 2014; 4 pages.

*Primary Examiner* — Justine R Yu
*Assistant Examiner* — Matthew D Ziegler
(74) *Attorney, Agent, or Firm* — VIA LLP

(57) ABSTRACT

Nasal cannulas for providing respiratory therapy to patients can have a curved prong section that has turbulation elements on the inside curve of the prong. A flow of breathing gas moving through the prong may incur less resistance and create less noise when flowing through such a prong due to the promotion of favorable flow dynamics.

16 Claims, 5 Drawing Sheets

(56)            References Cited

U.S. PATENT DOCUMENTS

| | | | |
|---|---|---|---|
| 7,493,902 | B2 | 2/2009 | White et al. |
| 8,110,267 | B2 | 2/2012 | Houston et al. |
| 8,136,527 | B2 | 3/2012 | Wondka |
| 8,225,796 | B2 | 7/2012 | Davenport et al. |
| 9,730,830 | B2* | 8/2017 | Foley .......................... A61F 5/08 |
| 10,933,210 | B2 | 3/2021 | Gulliver |
| 2004/0039351 | A1* | 2/2004 | Barrett .................... F16L 9/006 |
| | | | 604/246 |
| 2008/0172121 | A1 | 7/2008 | Scholz |
| 2009/0044808 | A1 | 2/2009 | Guney et al. |
| 2009/0045006 | A1 | 2/2009 | Kondo |
| 2009/0183739 | A1 | 7/2009 | Wondka |
| 2009/0320851 | A1* | 12/2009 | Selvarajan ........ A61M 16/0666 |
| | | | 128/207.13 |
| 2011/0232649 | A1 | 9/2011 | Collazo et al. |
| 2015/0165151 | A1 | 6/2015 | Payton et al. |
| 2016/0220775 | A1 | 8/2016 | Gulliver |

* cited by examiner

NASAL CANNULA WITH TURBULATION ELEMENTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure generally relates to systems and devices for providing gases to patients for respiratory therapy. More particularly, the present disclosure relates to nasal cannula interfaces for providing gases to patients via the nasal passages.

BACKGROUND

Medical professionals may wish to provide patients with respiratory assistance in the form of supplemental oxygen or airflow for many reasons in ICU, other hospital, or home environments. Different types of interfaces for supplying gases to patients are available. For example, various nasal masks, full face masks, oral interfaces, nasal pillows, and nasal cannula interfaces exist. Nasal cannula interfaces may include two nasal prongs that are placed in the patient's nostrils to deliver gases to the patient.

SUMMARY

A nasal cannula system typically comprises a cannula body defining a cavity, one or two prongs extending from the body, and gases supply tubing that extends from one or two sides of the body. In some prior art configurations, the prong may be curved rather than straight to better match the profile of the nares. However, as flow moves through a curved prong, the flow may develop turbulent eddies that may generate noise and increase resistance to flow. Thus, it is an object of the disclosure to provide patients with a nasal cannula that might be easier to use, or at least provide the public with a useful choice.

In some configurations, a nasal cannula comprises a cannula body defining a cavity and at least one curved nasal prong extending from the cannula. The prong has an interior passage in communication with the cavity. A turbulation element is on an inside curve of the prong.

In some configurations, the turbulation element is adapted to induce turbulence in a flow of breathing gas through the interior passage in a boundary layer at the inside curve.

In some configurations, the turbulation element extends along an entire length of a curved section of the prong.

In some configurations, the turbulation element extends along an entire circumferential length of the inside curve.

In some configurations, the turbulation element extends beyond the inside curve in a circumferential direction.

In some configurations, the turbulation element comprises a surface portion having a component that extends in a circumferential direction.

In some configurations, an initial portion of the prong extending from a portion of the cannula body defining the cavity is generally straight.

In some configurations, the turbulation element comprises a plurality of one or more of recesses, ridges, pits, protrusions, bumps, lumps or humps.

In some configurations, the turbulation element comprises random surface texturing.

In some configurations, features defining the turbulation element are elongated in a circumferential direction.

In some configurations, an average amplitude of features defining the turbulation element is between 0% and 5% of a diameter of the prong.

In some configurations, the prong is formed as a unitary structure with the cannula body.

In some configurations, the prong is formed separately from a portion of the cannula body that defines the cavity.

In some configurations, a nasal cannula system comprises a flow circuit defined by one or more of a source of breathing gas, a supply conduit and a cannula having at least one curved nasal prong. The flow circuit comprises a curved portion. At least one turbulation element is provided on an inside curve surface of the curved portion.

BRIEF DESCRIPTION OF THE DRAWINGS

Specific embodiments and modifications thereof will become apparent to those skilled in the art from the detailed description herein having reference to the figures that follow.

DETAILED DESCRIPTION

Figure 1:
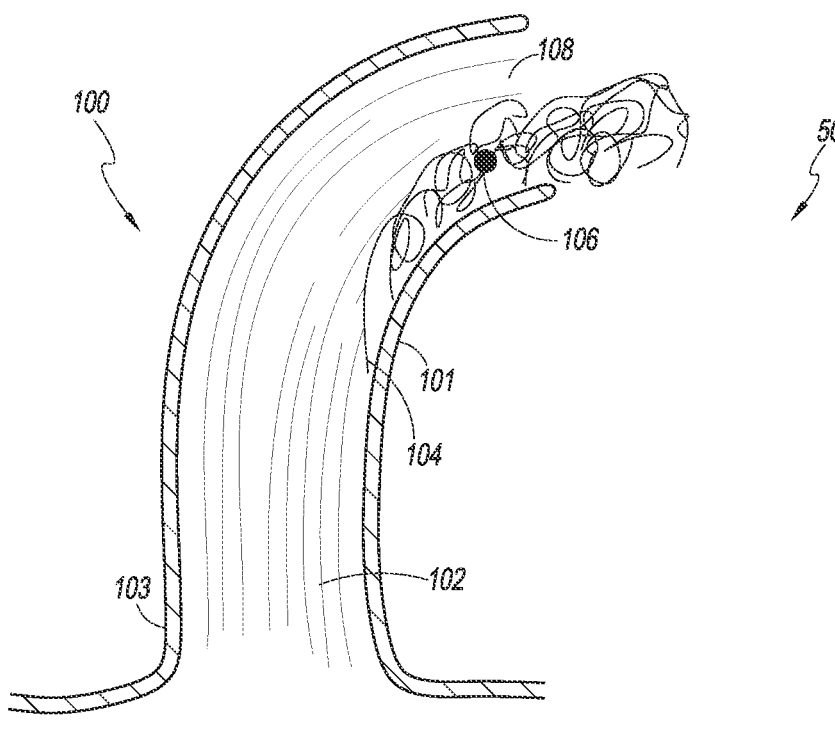
FIG. 1 is a side cross-sectional view of a nasal prong of a nasal cannula.

With reference to FIG. 1, a curved nasal cannula prong 100 with an initially laminar gas flow 102 moving through the prong 100 is shown. As laminar flow 102 passes through the relatively straight base 103 of the prong and into the more curved region 101, certain phenomena related to flow dynamics of the system can be observed. In this case, the flow may come to have a relatively low pressure on the inside of the curve and a relatively high pressure on the outside of the curve. In the low pressure area on the inside of the curve, the laminar flow in the boundary layer may be prone to flow separation at some point 104 along the flow path, which can separate the flow into a turbulent flow layer 106 and a laminar flow layer 108. An undesirable level of flow resistance and noise can arise from excessive turbulent flow like that present in the turbulent flow layer 106.

One way of mitigating the effects of the turbulent flow layer 106 is to place a turbulation element 110 on the surface of the inside curve of the prong 100. The turbulation element 110 may be or comprise one or a plurality of, for example, a pit, protrusion, recess, ridge, bump, lump, hump, and/or other element that may create a suitable surface roughness on the inside curve of the prong 100.

Figure 2:
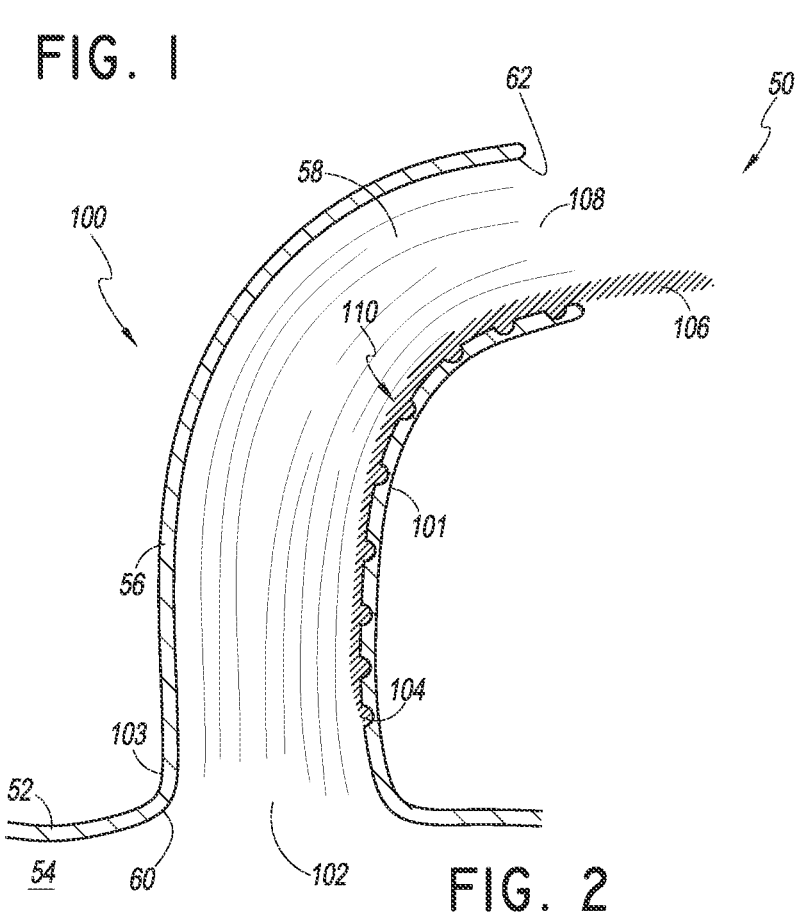
FIG. 2 is a side cross-sectional view of a nasal prong of a nasal cannula, wherein the prong comprises turbulation elements on the inside curve of the tube wall.

With reference to FIG. 2, a nasal cannula system 50 includes a cannula body 52 defining a cavity 54. The cannula body 52 can be held in place on the face of a user by any suitable arrangement, such as a headgear assembly or adhesive, for example. The cannula body 52 can be any size or shape suitable for being positioned on the face of the user and supporting one or two nasal prongs 100 for placement in the nares of the user. Similarly, the cavity 54 can be of any suitable size or shape for supplying a flow of breathing gas to the prongs 100. The flow of breathing gas can be provided by a gases source or generated by a blower, for example, and supplied to the cavity 54 by a suitable conduit, such as a breathing gas supply tube.

Each of the prongs 100 comprises a side wall 56 that defines an interior passage 58, which communicates with the cavity 54 to deliver the flow of breathing gas from the cavity 54 to the user's nares. The side wall 56 of the prongs 100 can be formed as a unitary structure with the cannula body 52 or can be formed separately, such as by a prong insert. The prongs 100 each have an opening at a first end, which is referred to as an inlet 60, and an opening at a second end, which is referred to as an outlet 62. The inlet 60 allows the flow of breathing gas to enter the passage 58 of the prong 100 from the cavity 54. The outlet 62 allows the flow of breathing gas to exit to passage 58 and the cannula system 50. Preferably, the side wall 56 comprises a curved portion such that the axes of the inlet 60 and outlet 62 or planes in which the inlet 60 and outlet 62 lie are non-parallel or angled relative to one another. The curved portion of the side wall 56 can define an inside curve or inside portion that is closest to the radius of the curve and an outside portion that is furthest from the radius of the curve. The curved portion can comprise a portion or an entirety of the side wall 56. In some configurations, an initial portion of the prong 100 extending from the cannula body 52 is generally straight or linear and a subsequent portion of the prong 100 is curved. Other features of the cannula system 50 can be similar to any of those disclosed in Applicant's application no. PCT/NZ2014/000040, filed Mar. 14, 2014, entitled NASAL CANNULA ASSEMBLIES AND RELATED PARTS, the entirety of which is incorporated by reference herein.

Whether used in a hospital environment or in a home environment, a system for providing a flow of gases to a patient or user may comprise four main pieces of apparatus. Firstly a blower for providing a flow of pressurised gas to the patient. Secondly an active humidifier that controls the temperature of a heater plate heating a body of water to achieve a desired temperature and humidity of the flow of gas. Thirdly a transport conduit from the humidifier to the patient is also required, which may be heated to reduce condensation, or "rain out". Fourthly a patient interface for delivering the pressurized humidified flow of gases to a patient, for example a nasal cannula designed to fit into the nasal cavity of a patient or user. In some situations a flow of pressurized gases may be provided to a patient without humidification, in which case a humidifier is not a necessary apparatus.

Nasal cannulas can be used to deliver a flow of gases to a patient and may either seal, semi-seal or not provide a seal at the nostrils of a patient. Nasal high flow (NHF) is typically a non-scaling therapy that delivers relatively high-volume flow to the patient through a patient interface such as a nasal cannula.

The preferred form of the nasal cannula 30 which forms part of the patient interface 20 shall now be described in more detail with particular reference to FIGS. 5, 6, 7, 8, and 9.

The nasal cannula 30 of the preferred form comprises two main parts: a manifold portion 35 and a face mount part 32. The preferred embodiments of these two parts will now be described with particular reference to FIGS. 5 and 6.

In the preferred form, the manifold portion 35 is in use connected to and in fluid communication with the secondary supply conduit 62 as has been described above. However, it could be connected directly to the main delivery conduit 3 in alternative embodiments. Where the phrase 'gases inlet manifold part' is used in this specification, this should be taken to mean the manifold portion 35 in combination with the secondary supply conduit 62, or just the manifold portion 35, as appropriate.

Figure 5:
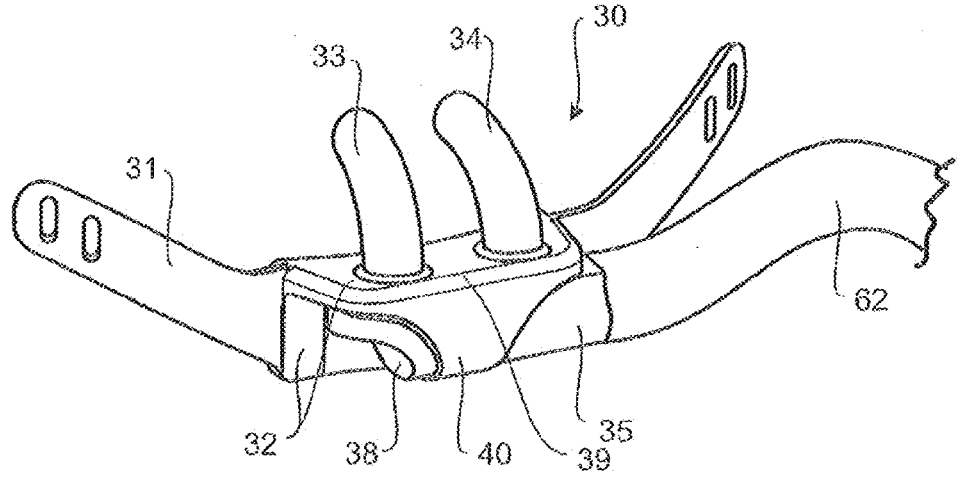
FIG. 5 shows a perspective view from the front and to one side of the most preferred form of nasal cannula, the nasal cannula of the preferred form having a face mount part and a manifold part, the manifold part removable from the face mount part, the secondary supply conduit connected to the manifold part.
Figure 6:
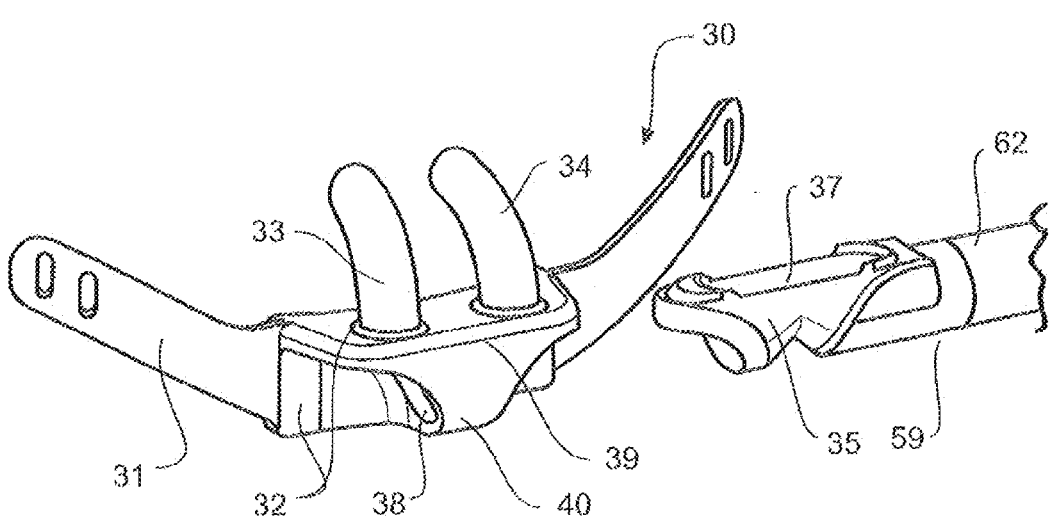
FIG. 6 shows the patient interface of FIG. 5 with the manifold part removed from the face mount part.

It should also be noted that the preferred form as shown in FIGS. 5 and 6 shows the manifold part 35 as being detachable from the remainder of the nasal cannula 30. However, the manifold part 35 could also be formed as an integral part of the nasal cannula 30 if preferred or required—that is, so that the manifold part 35 and the face mount part 32 (described below) are one item.

The preferred form of manifold part 35 is generally tubular in shape having a substantially circular inlet 59 on one side that curves to an elongated oval outlet 37, the outlet 37 being formed on one side of the manifold part 35 so that it is perpendicular to the inlet 59. The circular inlet 59 in the preferred form receives the patient end of the secondary supply conduit 62, such that the gases from the secondary supply conduit 62 can flow through the manifold part 35 (inlet 59 could alternatively be oval, or any other suitable shape—it does not have to be circular). In the preferred embodiment the manifold part 35 is integrated with the secondary supply conduit 62 (i.e. it is not intended to be removed and replaced repeatedly in use, although it can be removed if required), but alternatively the manifold part 35 could be removably attached to the secondary supply conduit 62, The manifold part 35 engages with the face mount part 32 so that gases can pass through the outlet 37 and transfer from the secondary supply conduit 62 to the patient 2 through the nasal prongs 33, 34 (described in detail below).

In the preferred embodiment the manifold part 35 is manufactured from a hard plastic material that only deforms under relatively high loading conditions (that is, it cannot easily be crushed in the hand of a user). The manifold part 35 may be moulded, injection moulded, machined or cast.

The manifold part 35 in use is connected to the face mount part 32, so that gases exiting the manifold part 35 enter the face mount part 32. The term "connected" in the context of this specification should be taken to mean either "detachable" or "integral with", as appropriate. The face mount part will now be described in detail.

The face mount part 32 includes the nasal prongs 33, 34, so gases passing through the face mount part 32 can enter the nasal prongs 33, 34 and be delivered to the patient 2. The preferred form of nasal prongs 33, 34 extend parallel to each other, curving upwards and inwards from the face mount portion 32. In the preferred embodiment, each nasal prong is equidistant from the centre of the face mount part. The structure of the prongs 33, 34 will be described in detail below.

Figure 4:
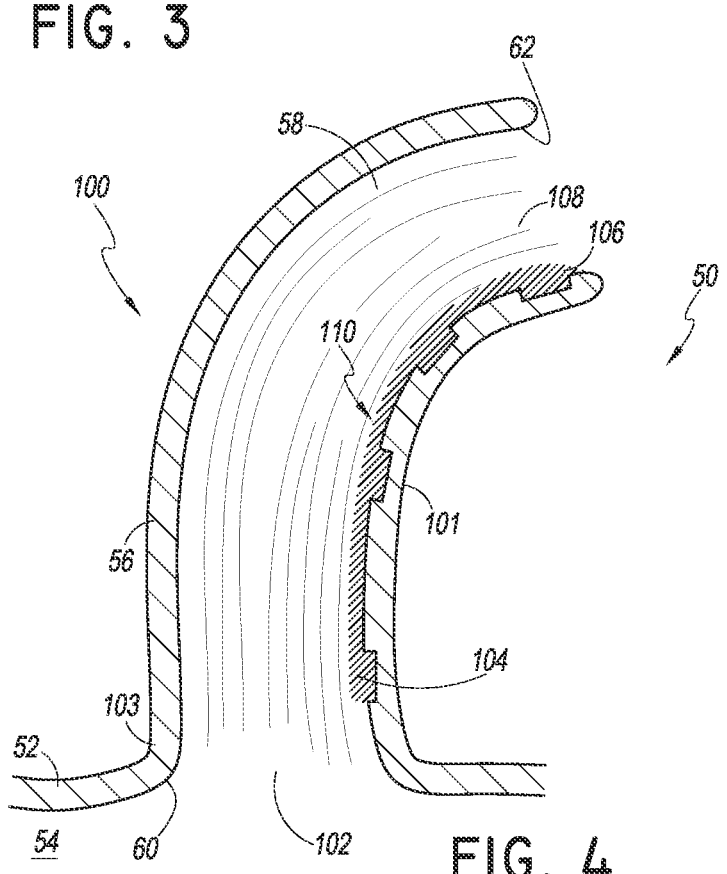
FIG. 4 is a side cross-sectional view of a nasal prong of a nasal cannula, where the prong comprises yet another alternative version of the turbulation elements on the inside curve of the tube wall.

The face mount part 32 of the preferred embodiment includes side straps 31 and an open tubular recess 38, integrally moulded together as shown in FIGS. 4 and 5. The open tubular recess 38 extends below the face mount part 32 and is adapted to receive the manifold part 35 (for the preferred embodiment where the face mount part 32 and the manifold part 35 are separable items). The face mount part 32 has a lip 39 that extends around the upper edge of the open tubular recess 38. The manifold 35 is connected to the face mount part 32 by a friction fit and the lip 39 on the face mount part 32 helps to grip the manifold part 35 and form a strong sealed connection between the manifold part 35 and the face mount part 32. The open tubular recess 38 is divided by a rib 40 which extends below the face mount part 32. The rib 40 helps to cradle and hold the manifold part 35 in the correct position as it engages with the face mount part 32, the rib 38 extending around the outside of the manifold part 35. Outlet 37 on the manifold part 35 aligns in use with the underside of the face mount 32 portion when the manifold part 35 is connected to the face mount part 32. This alignment minimises and reduces the amount of gases which leak out of the nasal cannula arrangement 30, allowing effective treatment of the user by delivering maximum amount of humidified gases.

The side straps 31 are used to attach the head strap 50 or the ear loops to the face mount part 32. The side straps 31 comprise a pair of straps (shown as straps 31 on the figures) which extend from either side of the face mount part 32, and which in the preferred embodiment are formed as an integral part of the face mount part 32. The headgear strap 50 is in use attached to the side straps 31 so that the patient interface can be worn by a user in use. In the preferred form the ends of the headgear strap 50 are looped through a pair of slits on the side straps 31, with the ends including velcro or similar to hold the ends in place when the y are looped back on themselves. Alternatively the headgear strap 50 or loops 66 may be clipped onto the side straps 31, for example by way of co-operating male-female clips, or adhesively attached to the side straps 31.

In the preferred embodiment the face mount part, nasal prongs, side straps and the open tubular recess are all manufactured as one continuous item. The face mount part 32, nasal prongs 33, 34, side straps 31 and the open tubular recess 38 are all manufactured out of flexible polymer material or silicone, preferably a soft thermoplastic elastomer (TPE).

The nasal cannula of the present disclosure can be used in high flow, high pressure therapy (e.g., high flow respiratory therapy). A stream of gases enters the manifold substantially horizontally because the cannula has a side entry manifold. The stream of gases flows from the manifold into the prongs, out of the top of the prongs and into a user's nostrils. The inlet stream of gases enters the manifold in a substantially horizontal direction that is approximately orthogonal to the prongs. The inlet stream of gases turns through approximately ninety degrees as the gases flow into and up the prongs such that the stream of gases flows substantially aligned with the prongs axis of extension relative to the manifold. In prior art nasal cannula a substantial amount of the gases generally changes direction or turns at the entry of the prongs, which is a small area at the base of the prongs. The turning of the stream of gases within the entry to the prong causes the velocity of the gases stream to reduce. The reduction in flow velocity causes a pressure drop across the entry of the prongs since the pressure of the gases stream is proportionally related to the velocity of the gases stream. In prior art cannula approximately 65% of the gases stream is turned within the entry of the prongs. The pressure drop is proportional to the radius of the prongs to the power of four. The pressure and velocity drop is undesirable because it reduces the effectiveness of the therapy being delivered to the patient. The reduced pressure and velocity may also be dangerous for the patient as the patient may not be getting enough breathing gases. In CPAP type treatment the airways of the patient need to be consistently pressurised in order to allow the patient to breathe properly. A reduction in gases stream pressure due to the pressure drop across the entry to the prongs can cause the airways of the patient to collapse due to lack of pressure being supplied to the patient. The reduction in pressure can also cause the blower speed and power to increase in order to compensate for the pressure drop. This can be dangerous because the blower may be operating at high speeds. The pressure and velocity drop can also be adverse to patients receiving ventilator therapy because these patients will not receive adequate breathing pressure and the ventilator can begin to operate outside normal operating levels to try and compensate for the pressure and velocity drop. The prior art cannula may suffer from a pressure drop of approximately 25 cm H2O.

Figure 7:
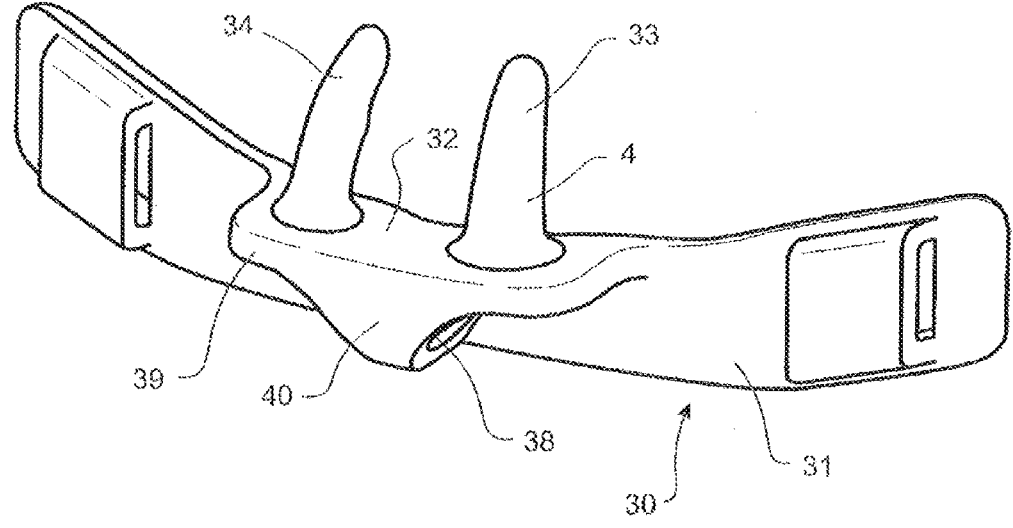
FIG. 7 shows a perspective view from the front and to one side of the preferred form of the face mount part of the preferred form of nasal cannula, the face mount part including a section adapted to receive the manifold part, and a pair of nasal prongs extending from the face mount part.
Figure 8:
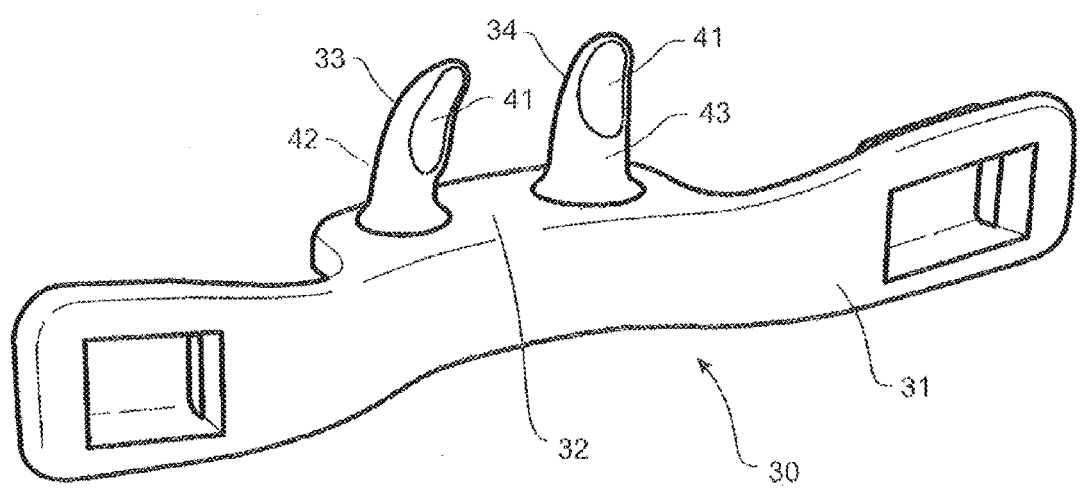
FIG. 8 shows a perspective view from the rear and to one side of the preferred form of the face mount part of the nasal cannula, the face mount part having a pair of nasal prongs extending from the face mount part, each of the nasal prongs having a gases exit cut-out on their rear face, at the upper part of the prong.
Figure 9:
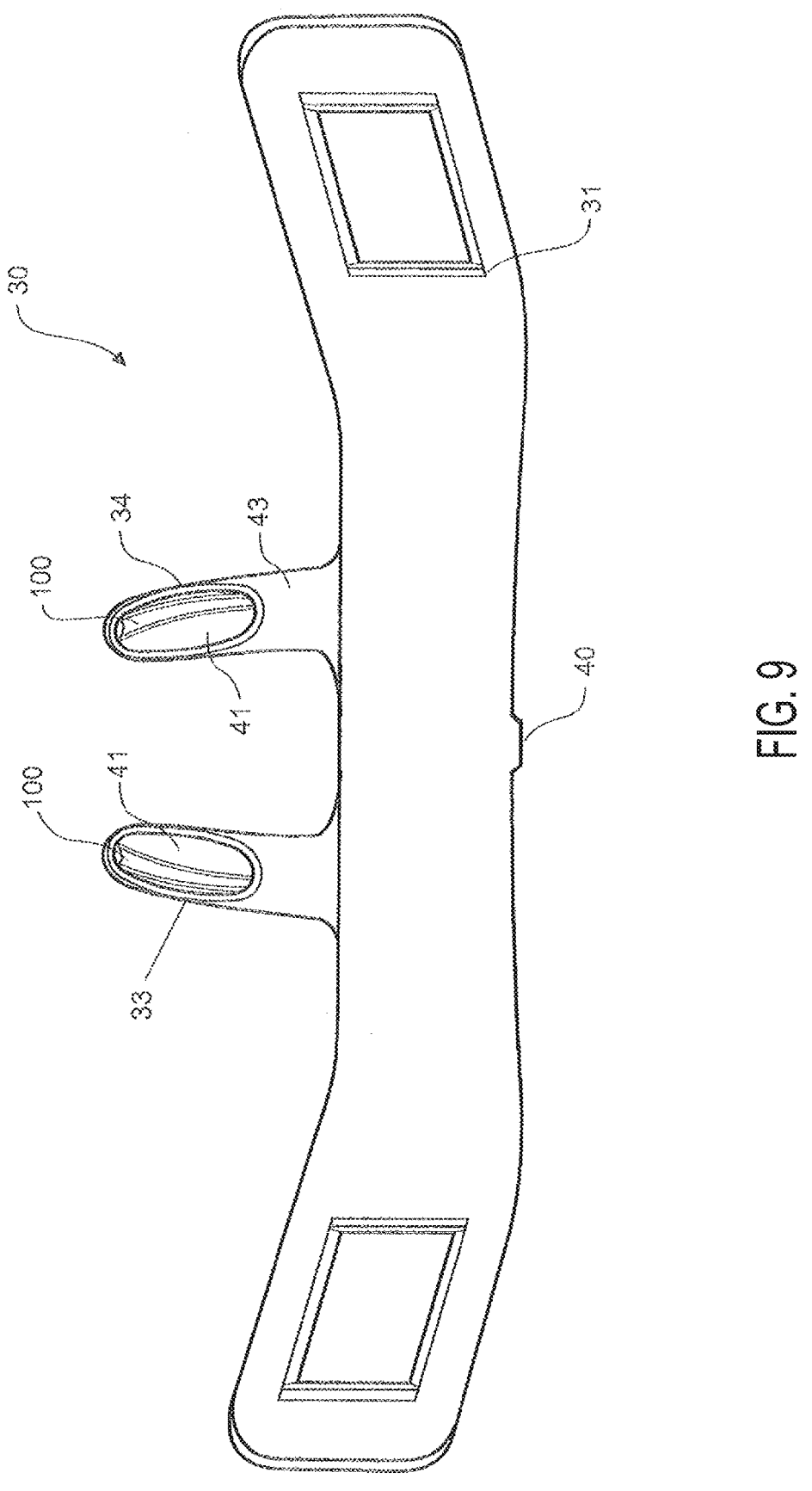
FIG. 9 shows a view directly from the rear of the manifold part of FIG. 5, with the gases exit cut-out clearly shown.

The nasal cannula arrangement 30 as shown in FIGS. 7 and 8 is suitable for the delivery of high airflow, high humidity gas flow to the patient's nasal cavity. In the preferred embodiment, the cut-out extends between from the top of the prong to between half and two thirds of the distance to provide the largest cut-out. Further, the shape of the cut-out (reverse S-shape surface as described above) contributes to ensuring maximum diffusion and reduction of air jetting effects.

In prior art cannulas, the cannula prongs will generally have an exit aperture which is substantially the same size as their inlet aperture (e.g. where the base of the prong is connected to a manifold). In the cannula of the present described above, the size and shape of the cut-out helps to reduce the air speed at the point of exit from the prong, and to direct the gases in a generally rearwards direction. It has been found that this helps to increase user comfort and compliance with a therapy regime to a surprising degree. Furthermore, the decreased velocity flow of respiratory gases from the cut-out 41 of the nasal prongs 33, 34 helps to ensure that the user will breathe as normally as possible.

The reduction in air velocity due to the cut-outs in the prongs 33, 34 allows the use of a higher flow rate than is generally the case in the prior art. In therapy, high flow rates are preferred in order to meet the patient's requirements. Using high flow rate ensures that where possible, the entire volume of an inhaled breath comprises respiratory gases. However, due to increased patient discomfort and potentially dangerous side-effects with higher flow rates, a trade-off is normally made between patient comfort/safety, and flow rate. Lower flow rates than may be optimal are used to ensure the patient is comfortable enough to conform to a therapy regime. Using these lower flow rate means at least part of, and generally a majority of, the user's breath is composed of ambient air which can be detrimental to the therapy provided by medical gases. Using relatively higher flow rates and having nasal prongs that allow humidified medical gases to be delivered at high flow rates is advantageous. This helps to ensure that the most efficient and effective therapy provided to a patient. Surprisingly, it has been found that by using the prongs as described above—i.e. prongs that include a cut-out section-flow rates between (but not limited to) just above 0 L/min to 80 L./min can be delivered to a user and initial user feedback suggests that there is decreased discomfort and a greater tendency towards regime compliance. The prongs can be re-sized—e.g. for use in neonatal applications—without departing from the scope of the, with the flow rates or flow range being considerably lower in neonatal applications. It is anticipated that flow rates of up to 120 L/min could be used in certain circumstances. However, it is anticipated that the preferred range will be in the order of 20-50 L/min for adults, 5-30 L/min for Paediatric patients, and just over 0 L/min to 8 L/min for Neonatal patients. The cut-out design is effective at low flow rates when used on neonatal patients (as small as 400 gms), where flow rates of 1-8 L/min would otherwise create very high velocities due to the small size of the cannula and patient.

In the illustrated configuration of FIG. 2, one possible arrangement of a turbulation element 110 comprises at least one and preferably a plurality of depressions/recesses or ridges defined between the depressions. The depressions or ridges are provided along a length of the inside of the curve of the prong 100. The depressions or ridges can be provided along a portion of the length of the curve of the prong 100 or along a substantial entirety or an entirety of the length of the curve of the prong 100. In some configurations, the depressions or ridges are provided along a substantial entirety or an entirety of the length of the prong 100.

The depressions or ridges can be provided on only a portion of the inside portion of the curve of the prong 100 in a circumferential direction or direction around a longitudinal axis of the passage 58 or side wall 56 of the prong 100. In other arrangements, the depressions or ridges can be provided on an entirety of the inside portion of the curve of the prong 100. In some arrangements, it may be desirable or at least not harmful to the performance of the cannula system 50 to provide depressions or ridges on both inside portions and outside portions of the curve of the prong 100. Thus, in some arrangements, an entire interior surface of the side wall 56 of the prong 100 can comprise depressions or ridges. In some configurations, it may be desirable to provide depressions or ridges only on an outside portion of the curve or to omit the depressions or ridges on an inside portion of the curve while providing depressions or ridges elsewhere.

The depressions or ridges of the turbulation element 110 can be of any number, size or shape suitable to induce a desirable or effective level of laminar flow in the prong 100 or to provide a desirable or effective reduction in eddy currents, such as by inducing a turbulent boundary layer at the inside curve. The depressions or ridges can be elongate and can extend in a circumferential direction (or around the longitudinal axis) of the passage 58 of the prong 100 or can be offset from a circumferential direction or a direction perpendicular to the longitudinal axis of the passage 58. The depressions or ridges can be of a relatively short length, including round or square, and can be provided in a repeated pattern in a circumferential direction or a direction perpendicular to the longitudinal axis of the passage 58. Preferably, the depressions or ridges have at least a surface portion having a component that extends in a circumferential direction or a direction perpendicular to the longitudinal axis of the passage 58.

The size of the turbulation element 110 (e.g., a depth of the depressions or a height of the ridges) can be related to or selected based on characteristics or dimensions of the passage 58 of the prong 100, such as a particular proportion of the cross-sectional width or diameter, the cross-sectional area, the length or the radius of curvature of the passage 58, for example. The size of the turbulation element 110 can be related to or selected based on the flow characteristics of the flow of breathing gas through the passage 58 of the prong 100. The turbulation element 110 can be sized based on a combination of these factors or in view of other relevant factors, such as manufacturability or material considerations, for example, or any combination thereof.

In some configurations, as incoming flow 102 moves through the prong 100, the turbulation element 110 induces turbulence in a thin section of the boundary layer on the inside curve of the prong 100 at and/or around the point 104 where the flow encounters or runs along the element 110. The thin turbulent flow layer 106 created is much less prone to separation from the inside curve of the prong 100 than laminar flow, and so a larger portion of the flow may remain laminar and/or a eddy currents are reduced relative to a prong 100 that does not comprise a turbulation element 110, which may decrease the flow resistance and noise of flow moving through the prong 100 in use.

Figure 3:
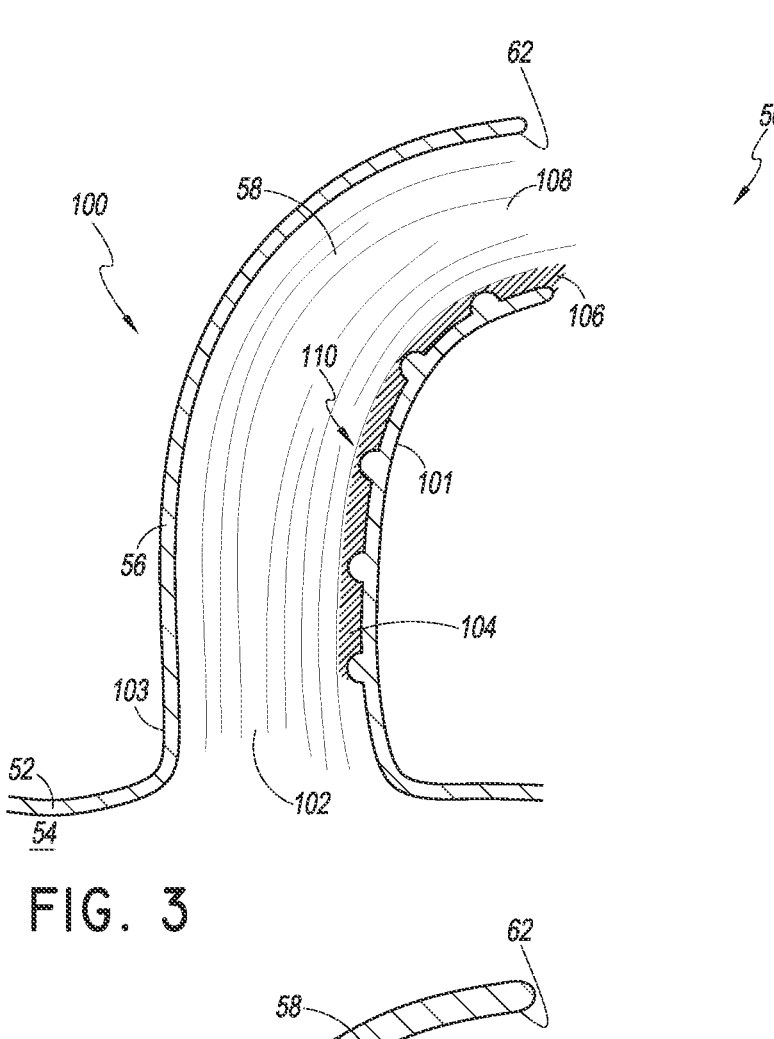
FIG. 3 is a side cross-sectional view of a nasal prong of a nasal cannula, wherein the prong comprises an alternative version of the turbulation elements on the inside curve of the tube wall.

There are no particular limitations as to the size, shape, number or arrangement of the individual features defining the turbulation element 110. Some possible configurations of the turbulation elements 110 are shown in FIGS. 3 and 4. Features or characteristics of such turbulation elements 110 or of the cannula systems in general can be the same as or similar to those described elsewhere herein or can be of any other suitable arrangement.

With reference to FIG. 3, the turbulation element 110 comprises at least one and preferably a plurality of raised bumps. The raised bumps can be, for example, a portion of a sphere, ovoid, cube, cuboid, cone, cylinder or other geometric shape. The number, size, shape and other characteristics can be selected as desired or as described herein.

With reference to FIG. 4, the turbulation element 110 comprises at least one and preferably a plurality of ridges and recesses. The ridges or recesses can be, for example, a portion of a sphere, ovoid, cube, cuboid, cone, cylinder or other geometric shape. The number, size, shape and other characteristics can be selected as desired or as described herein.

In some configurations, the turbulation element 110 may comprise an ordered or random surface texture/roughness along a portion or an entirety of the inside curve of the prong 100. In a preferred configuration, the average amplitude of the surface roughness Ra of the turbulation element 110 is between about 0% and 5% of the diameter (or other cross-sectional dimension) of the prong 100. In some configurations, the turbulation element 110 may instead be any feature that promotes a thin turbulent boundary layer on the inside curve of the prong 100. In some configurations, the element 110 is integrally formed with the cannula prong 100. In some configurations, the element 110 is a component separate from the cannula prong 100. In some configurations, the element 110 may be placed on any inside curve of the prong 100. In some configurations, the element 110 may circumscribe the internal walls of the prong 100. Additionally, such turbulation elements 110 may be beneficially placed anywhere in which there is a curved section in the flow path of the cannula circuit, e.g., prongs, curved parts of the gases supply tube, within the flow generator/flow source, in the gases flow manifold/prong transition, et cetera.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of an embodiment of the present invention have been described with reference to nasal cannulas. However, certain features, aspects and advantages of the nasal cannulas as described above may be advantageously used with other therapeutic or non-therapeutic breathing interfaces, such as full face masks, nasal masks, oral masks, and nasal pillows. Certain features, aspects and advantages of the method and apparatus of the present disclosure may be equally applied to other breathing devices for other conditions.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A system for providing gases for high flow respiratory therapy, comprising:

a gases flow source for providing high flow respiratory therapy, the gases flow source is configured to provide flow rates greater than 20 L/min;

a humidifier;

a nasal cannula comprising:

a cannula body defining a cavity and a pair of nasal prongs extending from the nasal cannula, the pair of nasal prongs being configured to not seal with a nare of a user, each of the pair of nasal prongs having an interior passage in communication with the cavity, a plurality of turbulation elements, wherein the plurality of turbulation elements are configured to induce turbulence in the gases in a boundary layer adjacent to the plurality of turbulation elements, wherein the interior passage comprises a first region defining an inside curve and a second region defining an outside curve, wherein the plurality of turbulation elements are positioned entirely within only the first region or entirely only within the second region and are located on an inner surface of each of the pair of nasal prongs;

wherein each of the plurality of turbulation elements are positioned within a gas flow path of each of the pair of nasal prongs;

wherein each of the plurality of turbulation elements are formed along a bulk flow path or an inspiratory flow path;

wherein each of the plurality of turbulation elements are configured to reduce flow resistance and reduce noise of an inspiratory gases flow;

and wherein the first region or the second region that does not contain the plurality of turbulation elements does not cause turbulence.

2. The system of claim 1, wherein the plurality of turbulation elements are positioned on at least one surface of the gas flow path in the system.

3. The system of claim 1, wherein the nasal cannula further comprises a manifold configured to provide a flow of gases to the pair of nasal prongs.

4. The system of claim 3, wherein the manifold is removable from the nasal cannula.

5. The system of claim 1, wherein the system further comprises a cannula that extends from a lateral side of the nasal cannula.

6. The system of claim 1, wherein the pair of nasal prongs are curved.

7. The system of claim 1, wherein the gases flow source comprises a blower.

8. The system of claim 1, wherein the plurality of turbulation elements comprise a plurality of one or more of recesses, ridges, pits, protrusions, bumps, lumps, or humps.

9. The system of claim 1, wherein the plurality of turbulation elements comprise random surface texturing.

10. The system of claim 1, wherein features defining the plurality of turbulation elements are elongated in a circumferential direction.

11. The system of claim 1, wherein an average amplitude of features defining the plurality of turbulation elements is between 0% and 5% of a diameter of at least one of the pair of nasal prong.

12. The system of claim 1, wherein the pair of nasal prongs are formed as a unitary structure with the cannula body.

13. The system of claim 1, wherein the pair of nasal prongs are formed separately from a portion of the cannula body that defines the cavity.

14. The system of claim 1, wherein the plurality of turbulation elements are positioned within both of the pair of nasal prongs.

15. A system for providing gases for high flow respiratory therapy, comprising:

a gases flow source for providing high flow respiratory therapy, the gases flow source is configured to provide flow rates greater than 20 L/min;

a humidifier;

a nasal cannula comprising:

a cannula body defining a cavity and at least one nasal prong extending from the nasal cannula, the at least one nasal prong being configured to not seal with a nare of a user, each nasal prong of the at least one nasal prong having an interior passage in communication with the cavity, and a plurality of turbulation elements comprising a plurality of one or more recesses, wherein the plurality of turbulation elements are configured to induce turbulence in the gases in a boundary layer adjacent to the plurality of turbulation elements;

wherein the plurality of turbulation elements are located on an inner surface of the at least one nasal prong, wherein the inner surface comprises a first region defining an inside curve and a second region defining an outside curve;

wherein the plurality of turbulation elements are positioned within a gas flow path of each of the at least one nasal prong;

wherein each of the plurality of turbulation elements are formed along a bulk flow path or an inspiratory flow path;

wherein each of the plurality of turbulation elements are configured to reduce flow resistance and reduce noise of an inspiratory gases flow;

wherein the plurality of turbulation elements are positioned entirely within only the first region or the second region;

and wherein the first region or the second region that does not contain the plurality of turbulation elements does not cause turbulation.

16. The system of claim 14, wherein the cannula body comprises a pair of nasal prongs, and the plurality of turbulation elements are positioned within both of the pair of nasal prongs.

\* \* \* \* \*